United States Patent [19]

Franek et al.

[11] Patent Number: 4,714,721

[45] Date of Patent: Dec. 22, 1987

[54] COMPOSITE PLASTICS-BASED MATERIAL FOR PROSTHESIS PURPOSES

[75] Inventors: Henning Franek, Braunfels-Tiefenbach; Heinz Broemer, Wetzlar; Klaus Deutscher, deceased, late of Wetzlar, by Anneliese Deutscher, heir; Roland Schaefer, Friedrichsdorf, all of Fed. Rep. of Germany

[73] Assignee: Ernst Leitz Wetzlar GmbH, Wetzlar, Fed. Rep. of Germany

[21] Appl. No.: 842,259

[22] PCT Filed: May 22, 1985

[86] PCT No.: PCT/DE85/00172

§ 371 Date: Feb. 5, 1986

§ 102(e) Date: Feb. 5, 1986

[87] PCT Pub. No.: WO86/00021

PCT Pub. Date: Jan. 3, 1986

[30] Foreign Application Priority Data

Jun. 7, 1984 [DE] Fed. Rep. of Germany ....... 3421157

[51] Int. Cl.$^4$ .................. A61K 6/06; A61K 49/04; A61L 25/00

[52] U.S. Cl. .................... 523/113; 523/117; 524/403

[58] Field of Search ................. 523/117, 113; 524/403

[56] References Cited

U.S. PATENT DOCUMENTS

| | | | |
|---|---|---|---|
| 3,922,430 | 11/1975 | Mayer | 428/323 |
| 3,955,295 | 5/1976 | Mayer | 428/323 |
| 4,059,628 | 11/1977 | Pesco et al. | 502/303 |
| 4,174,334 | 11/1979 | Bertenshaw et al. | 260/29.6 |
| 4,297,266 | 10/1981 | Ibsen | 523/115 |
| 4,388,373 | 6/1983 | Longo et al. | 523/440 |
| 4,407,984 | 10/1983 | Ratcliffe et al. | 523/115 |
| 4,460,705 | 7/1984 | Terauchi et al. | 502/303 |
| 4,500,657 | 2/1985 | Kumar | 523/117 |
| 4,503,169 | 3/1985 | Randklev | 523/115 |
| 4,540,723 | 9/1985 | Ying | 523/116 |
| 4,563,486 | 1/1986 | Nemcek et al. | 523/116 |

FOREIGN PATENT DOCUMENTS

| | | | |
|---|---|---|---|
| 0102199 | 3/1984 | European Pat. Off. | |
| 2370468 | 6/1978 | France | |
| 2086398 | 5/1982 | United Kingdom | 523/117 |

Primary Examiner—Herbert J. Lilling
Attorney, Agent, or Firm—Schwartz, Jeffery, Schwaab, Mack, Blumenthal & Evans

[57] ABSTRACT

Composite materials for prosthesis purposes are indicated, which consist of a plastics matrix and an inorganic radiopaque filler which, as the essential components, contains a combination of compounds of the elements Gd, Sr and, if appropriate, La. The proportion of filler in the total composite material is between 20 and 90% by weight.

The filler particles are in a silanized form of glass and/or glass ceramics and/or a sintered product and/or in the form of a mixture of their starting components and comprise (in % by weight): 1–31 of $Gd_2O_3$, 7–32 of SrO, 0–18 of $La_2O_3$, 14–62 of $SiO_2$, 0–30 of $B_2O_3$, 1–33 of $Al_2O_3$ and 0–16 of $Na_2$. A partial replacement of one or more of the radiopacity-causing compounds ($Gd_2O_3$ SrO, $La_2O_3$) by oxides of the elements Ca, Mg, Y, Zr, Ti, Ta and/or Nb is possible. In addition to the radiopaque filler, a composite material precursor contains at least one acrylate and/or methacrylate and a polymerization catalyst. The proposed composite material or its precursor is used above all in the dental field or as a bone cement.

26 Claims, No Drawings

COMPOSITE PLASTICS-BASED MATERIAL FOR PROSTHESIS PURPOSES

BACKGROUND OF THE INVENTION

The application relates to a plastics-based composite material for prosthesis purposes, which contains fillers of high X-ray absorption, based on glassy or glass-ceramic systems.

Plastics-based composite materials (or composites) have gained increasing importance in the recent past. Additions of inorganic fillers to polymerizable organic binders not only reduce shrinkage on polymerization, but also improve the mechanical strength data such as, for example, the compressive strength, the flexural strength and the modulus of elasticity. At the same time, the co-efficient of thermal expansion of the composite is also reduced as compared with that of the pure plastics.

The total composite system can be provided with the specific properties of the particular fillers used by the addition of inorganic fillers to organic binders. Thus, for example, in polymethyl methacrylate (PMMA) which is used for prothesis purposes, it was possible to transfer the property of forming a bond free of connecting tissues between bioactive implant material and bones to this system by introducing bioactive glass ceramics in a granular form into the PMMA; in this connection, compare German Pat. No. 2,501,683.

Furthermore, U.S. Pat. No. 3,066,112 has disclosed, in plastics-based dental materials, the replacement of methyl methacrylate by the reaction product of glycidyl methacrylate and bisphenol A, namely bis-[4-(2-hydroxy-3-methacryloyloxypropoxy)-phenyl]-dimethylmethane (also called bis-GMA) and the addition of quartz powder, treated with a vinylsilane, as an inorganic filler.

If the chemical composition is suitable, the inorganic filler can also be used for providing the plastics, which by their nature are permeable to X-rays, with the property of X-ray absorption, so that they become visible on the X-ray film. U.S. Pat. No. 3,539,526 has disclosed the use of a finely particulate glass prepared from $SiO_2$, $BaF_2$, $Al_2O_3$ and $B_2O_3$ as a radiopaque additive in tooth-filling material. These fillers frequently contain a high proportion of barium; however, their X-ray absorption is not sufficiently high for employing them successfully in composite materials which are used in the posterior tooth region. Known composites with barium-containing fillers reach a radiopacity of about 200%.

In addition, radiopause glasses are also known, the X-ray absorption of which is provided by the addition of compounds of strontium and lanthanum or of strontium or tungsten, cf. German Offenlegungsschrift No. 2,458,380. However, the X-ray absorption of even these glasses is not sufficiently high for using them in the preparation of a composite material of sufficiently high radiopacity for the posterior tooth region.

SUMMARY OF THE INVENTION

It is therefore the object of the present invention to provide a plastics-based composite material for prothesis purposes with the highest possible radiopacity and excellent mechanical data (compressive strength and flexural strength). The use of the composite material for medical purposes makes additional demands on the filler, since exclusion of any toxic constituents and adequate chemical stability to body fluids must be demanded in general and in the mouth environment in particular. In the use of a dental material—for example for artificial tooth crowns or bridges—there are additional requirements for good translucency and good polishability. For orthopedic applications—for example as a bone cement—the low viscosity of the organic binders must be preserved in spite of the addition of the fillers, in order to ensure good flow properties and optimum anchorability even in spongy bone material.

DETAILED DESCRIPTION OF PREFERRED EMBODIMENTS

The object is achieved, according to the invention, by a plastics-based composite material, containing a radiopaque filler, for prosthesis purposes, the radiopaque filler containing compounds of the elements gadolinium (Gd), strontium (Sr) and, if appropriate, lanthanum (La) as the component combination which causes X-ray absorption. Advantageously, the radiopaque filler contains the oxide group gadolinium oxide $(Gd_2O_3)$+strontium oxide (SrO) or gadolinium oxide $(Gd_2O_3)$+strontium oxide $(Sr_O)$+lanthanum oxide $(La_2O_3)$. The proportion of the radiopaque filler in the total composite material can be between 20 and 90% by weight, preferably 40 to 85% by weight.

According to a further embodiment of the present invention, the radiopaque filler comprises 1 to 31% by weight of gadolinium oxide $(Gd_2O_3)$, 7 to 32% by weight of strontium oxide (SrO) and 0 to 18% by weight of lanthanum oxide $(La_2O_3)$, the sum of the oxides $Gd_2O_3+SrO+La_2O_3$ being between 24 and 40% by weight; 14 to 62% by weight of silica $(SiO_2)$, 0 to 30% by weight of boron trioxide $(B_2O_3)$ and 1 to 33% by weight of alumina $(Al_2O_3)$, the sum of the oxides $SiO_2+B_2O_3+Al_2O_3$ being between 42 and 75% of weight; and 0 to 16% by weight of sodium oxide $(Na_2O)$. It is possible to replace the SrO proportion either by calcium oxide (CaO) up to 18% by weight or by magnesium oxide (MgO) up to 5% by weight. It is also within the scope of the present invention to replace the proportion of $Gd_2O_3$ and/or $La_2O_3$ and/or SrO by zirconium dioxide $(ZrO_2)$ up to 5% by weight. Finally, the formulation can also be modified in such a way that the proportion of $Gd_2O_3$ and/or $La_2O_3$ and/or SrO is replaced up to 5% by weight by at least one of the oxides yttrium oxide $(Y_2O_3)$, titanium dioxide $(TiO_2)$, tantalum oxide $(Ta_2O_5)$ and niobium oxide $(Nb_2O_5)$. A suitable composition of the radiopaque filler comprises: 1.0 to 26.9% by weight of $Gd_2O_3$, 10.9 to 28.8% by weight of SrO, 0 to 12.0% by weight of $La_2O_3$, 16.1 to 58.0% by weight of $SiO_2$, 0 to 26.3% by weight of $B_2O_3$, 2.0 to 32.0% by weight of $Al_2O_3$, 0 to 16.0% by weight of $Na_2O$, 0 to 15.0% by weight of CaO, 0 to 4.0% by weight of MgO, 0 to 5.0% by weight of $ZrO_2$, 0 to 5.0% by weight of $Y_2O_3$, 0 to 4.0% by weight of $TiO_2$, 0 to 5.0% by weight of $Ta_2O_5$ and 0 to 5.0% by weight of $Nb_2O_5$. According to a special embodiment of the present invention, the radiopaque filler comprises 2.0 to 10.0% by weight of $Gd_2O_3$, 15.0 to 25.0% by weight of SrO, 1.0 to 10.0% by weight of $La_2O_3$, 50.0 to 60.0% by weight of $SiO_2$, 2.0 to 6.0% by weight of $B_2O_3$, 1.0 to 3.0% by weight of $Al_2O_3$, 2.0 to 8.0% by weight of $Na_2O$ and 1.0 to 5.0% by weight of CaO. The radiopaque filler can be in the form of a glass having a refractive index $n_e$ of between 1.55 and 1.62 and/or in the form of glass ceramics and/or in the form of a sintered product and/or in the form of a mixture (blend) of its starting components.

The composite material according to the invention can additionally contain pigments of a particle size of less than 2 μm. It is advantageous for the radiopaque filler to be in the form of silanized particles. The particle size is in the range between 0.5 to 50 μm. It has proved to be advantageous for the composite material to contain additionally up to 30% by weight of highly disperse silica ($SiO_2$) and/or alumina ($Al_2O_3$). The precursor for the composite material can contain at least one acrylate and/or methacrylate as an organic binder as well as the radiopaque filler. In addition, a polymerization catalyst, in particular a photopolymerization catalyst, can be added to the precursor. This precursor or this composite material can advantageously be used as a dental material, in particular as a tooth-filling material. The use of the precursor as a bone cement is likewise possible.

It is very important to observe the refractive index interval, according to the invention, of the glassy filler for an application in the dental field, in order to obtain an aesthetic effect. The pasty precursors obtained by mixing the radiopaque filler with the organic binders have good plasticity. They are tack-free and can therefore be processed readily. In this case, it has proved to be particularly advantageous to silanize the inorganic filler by treatment with coupling reagents, for example vinylsilanes—in particular γ-methacryloyloxy-propyl-trimethoxysilane or vinyltriethoxysilane—as disclosed by German Pat. No. 1,937,871.

All the compounds known for these purposes can be used as the polymerizable binders. Acrylates and methacrylates of monohydric and polyhydric alcohols, for example the known bis-GMA and the so-called urethane-acrylates and -methacrylates known from German Offenlegungsschrift No. 2,312,559, are preferred to medical applications.

The polymerization or curing of the precursor according to the invention can take place at room temperature (cold polymerization), while hot (hot polymerization) or also by irradiation with visible light or UV light (photopolymerization) with the addition of suitable catalysts.

Examples of such catalysts are dibenzoyl peroxide/N,N-dimethyl-p-toluidine for cold polymerization, dibenzoyl peroxide for hot polymerization and benzil/N,N-dimethylaminoethyl methacrylate or benzoin methyl ether for photopolymerization.

With the proposed filler composition, a markedly improved composite material is made available; it has a very high X-ray absorption. A trial composite having a filler content of about 75% by weight has a radiopacity of about 350%.

For the case of use in the dental field, the translucency and the aesthetic effect of the composite material very largely corresponds to the values of the natural tooth material. It is stable in physiological-chemical terms and can readily be worked mechanically, in particular polished and ground.

The tables which follow give individual formulations for the radiopaque filler of the composite material according to the invention in percent by weight (% by weight). Table 1 gives the formulations of 35 individual examples, the oxides of the monovalent or divalent Na, Mg and Ca also appearing in addition to the component groups $SiO_2$, $B_2O_3$, $Al_2O_3$ and $Gd_2O_3$, SrO, $La_2O_3$.

Table 2 gives 10 further formulations of individual examples which, in addition to the two essential component groups, also contain oxides of trivalent to pentavalent metals. Finally, the refractive index $n_e$ was also shown.

TABLE 1

| (% by weight) | | | | | | | | | | | | |
|---|---|---|---|---|---|---|---|---|---|---|---|---|
| Example No. | 1 | 2 | 3 | 4 | 5 | 6 | 7 | 8 | 9 | 10 | 11 | 12 |
| $SiO_2$ | 23.66 | 24.00 | 24.36 | 25.18 | 25.30 | 25.28 | 25.07 | 26.71 | 26.94 | 27.87 | 16.30 | 16.18 |
| $B_2O_3$ | 20.38 | 20.68 | 21.00 | 21.10 | 22.00 | 22.01 | 21.82 | 21.47 | 23.24 | 24.88 | 21.95 | 21.77 |
| $Al_2O_3$ | 20.65 | 21.55 | 22.46 | 22.58 | 22.66 | 23.86 | 23.66 | 13.97 | 15.25 | 16.78 | 31.03 | 30.77 |
| $Gd_2O_3$ | 8.16 | 6.21 | 4.20 | 4.23 | 4.24 | 4.24 | 12.62 | 16.56 | 16.69 | 12.96 | 7.88 | 15.64 |
| SrO | 19.82 | 20.12 | 20.42 | 19.32 | 18.18 | 16.98 | 16.83 | 21.29 | 17.88 | 18.51 | 15.76 | 15.64 |
| $La_2O_3$ | 7.33 | 7.44 | 7.56 | 7.59 | 7.62 | 7.63 | — | — | — | — | 7.08 | — |
| $Na_2O$ | — | — | — | — | — | — | — | — | — | — | — | — |
| MgO | — | — | — | — | — | — | — | — | — | — | — | — |
| CaO | — | — | — | — | — | — | — | — | — | — | — | — |
| $n_e$ | 1.585 | 1.580 | 1.576 | 1.576 | 1.572 | 1.569 | 1.568 | 1.587 | 1.576 | 1.569 | 1.589 | 1.583 |
| Example No. | 13 | 14 | 15 | 16 | 17 | 18 | 19 | 20 | 21 | 22 | 23 | 24 |
| $SiO_2$ | 16.81 | 25.97 | 26.15 | 26.09 | 25.61 | 24.16 | 40.00 | 50.00 | 50.00 | 50.00 | 50.00 | 50.00 |
| $B_2O_3$ | 23.40 | 20.37 | 22.57 | 26.32 | 23.62 | 22.87 | 4.00 | 4.00 | — | — | 4.00 | 5.00 |
| $Al_2O_3$ | 31.98 | 25.47 | 14.81 | 16.70 | 15.62 | 15.12 | 2.00 | 2.00 | 2.00 | 2.00 | 2.00 | 3.00 |
| $Gd_2O_3$ | 6.09 | 2.21 | 20.26 | 1.14 | 23.81 | 26.88 | 5.00 | 5.00 | 5.00 | 5.00 | 5.00 | 5.00 |
| SrO | 16.25 | 23.99 | 16.21 | 28.72 | 11.34 | 10.97 | 21.00 | 20.00 | 20.00 | 20.00 | 20.00 | 20.00 |
| $La_2O_3$ | 5.47 | 1.99 | — | 1.03 | — | — | 8.00 | 8.00 | 8.00 | 8.00 | 8.00 | 7.00 |
| $Na_2O$ | — | — | — | — | — | — | 16.00 | — | — | 4.00 | 5.00 | 5.00 |
| MgO | — | — | — | — | — | — | 4.00 | — | — | — | — | — |
| CaO | — | — | — | — | — | — | — | 11.00 | 15.00 | 11.00 | 6.00 | 5.00 |
| $n_e$ | 1.583 | 1.566 | 1.580 | 1.570 | 1.580 | 1.590 | 1.585 | 1.601 | 1.618 | 1.606 | 1.591 | 1.589 |
| Example No. | 25 | 26 | 27 | 28 | 29 | 30 | 31 | 32 | 33 | 34 | 35 | |
| $SiO_2$ | 54.08 | 58.00 | 57.00 | 57.00 | 57.00 | 57.00 | 54.00 | 50.00 | 52.00 | 54.00 | 55.00 | |
| $B_2O_3$ | 4.08 | 4.00 | 4.00 | 4.00 | 4.00 | 4.00 | 3.50 | 3.50 | 3.50 | 4.00 | 4.00 | |
| $Al_2O_3$ | 2.04 | 2.00 | 2.00 | 2.00 | 2.00 | 2.00 | 2.00 | 2.00 | 2.00 | 2.00 | 2.00 | |
| $Gd_2O_3$ | 5.10 | 4.00 | 4.00 | 6.00 | 9.00 | 6.00 | 6.00 | 6.00 | 6.00 | 5.00 | 6.00 | |
| SrO | 20.41 | 20.00 | 20.00 | 20.00 | 20.00 | 18.00 | 20.00 | 20.00 | 20.00 | 22.00 | 20.00 | |
| $La_2O_3$ | 6.13 | 6.00 | 6.00 | 4.00 | 1.00 | 6.00 | 8.00 | 12.00 | 10.00 | 6.00 | 6.00 | |
| $Na_2O$ | 4.08 | 4.00 | 5.00 | 5.00 | 5.00 | 5.00 | 5.00 | 5.00 | 5.00 | 5.00 | 5.00 | |
| MgO | — | — | — | — | — | — | — | — | — | — | — | |
| CaO | 4.08 | 2.00 | 2.00 | 2.00 | 2.00 | 2.00 | 1.50 | 1.50 | 1.50 | 2.00 | 2.00 | |

TABLE 1-continued

| | | | | | (% by weight) | | | | | |
|---|---|---|---|---|---|---|---|---|---|---|
| $n_e$ | 1.576 | 1.558 | 1.560 | 1.560 | 1.558 | 1.559 | 1.573 | 1.589 | 1.585 | 1.573 | 1.569 |

TABLE 2

(% by weight)

| Example No.: | 36 | 37 | 38 | 39 | 40 |
|---|---|---|---|---|---|
| $SiO_2$ | 23.64 | 23.64 | 24.36 | 16.81 | 26.09 |
| $B_2O_3$ | 20.38 | 20.38 | 21.00 | 23.40 | 26.33 |
| $Al_2O_3$ | 20.65 | 20.65 | 22.46 | 31.97 | 16.70 |
| $Gd_2O_3$ | 8.00 | 6.33 | 3.18 | 5.50 | 2.00 |
| SrO | 19.00 | 19.00 | 21.00 | 14.32 | 23.85 |
| $La_2O_3$ | 4.33 | 6.00 | 3.00 | 6.00 | 1.03 |
| $Y_2O_3$ | — | — | — | — | — |
| $TiO_2$ | 4.00 | 4.00 | — | — | — |
| $ZrO_2$ | — | — | — | — | — |
| $Nb_2O_5$ | — | — | — | — | 4.00 |
| $Ta_2O_5$ | — | — | 5.00 | 2.00 | — |

| Example No.: | 41 | 42 | 43 | 44 | 45 |
|---|---|---|---|---|---|
| $SiO_2$ | 25.28 | 24.16 | 26.15 | 24.36 | 24.36 |
| $B_2O_3$ | 22.01 | 22.87 | 22.57 | 21.00 | 21.00 |
| $Al_2O_3$ | 23.86 | 15.12 | 14.81 | 22.46 | 22.46 |
| $Gd_2O_3$ | 4.00 | 20.88 | 14.47 | 4.20 | 4.20 |
| SrO | 14.85 | 10.97 | 17.00 | 20.42 | 20.42 |
| $La_2O_3$ | 7.50 | 1.00 | 2.50 | 5.06 | 2.56 |
| $Y_2O_3$ | — | 5.00 | 2.50 | — | — |
| $TiO_2$ | — | — | — | — | — |
| $ZrO_2$ | — | — | — | 2.50 | 5.00 |
| $Nb_2O_5$ | 2.50 | — | — | — | — |
| $Ta_2O_5$ | — | — | — | — | — |

The solubility of these inorganic fillers is very low. After treatment in water for 20 days at temperatures of 37° C., only weight losses of less than 0.1% result.

It has been found, surprisingly, that the use of a gadolinium compound together with a strontium compound or with a mixture of an Sr compound and an La compound within the indicated limits leads in the radiopaque filler to a superior overall absorption range—that is to say to a considerable increase in the radiopacity of the material as compared with the prior inorganic X-ray contrast substances.

To adjust the particular desired refractive index, the SrO can be partially replaced by the alkaline earth oxides CaO and/or MgO. The radiopacity-causing group of three ($Gd_2O_3+SrO$ or $Gd_2O_3+SrO+La_2O_3$) can also be replaced up to 5% by weight by $ZrO_2$ or, within the limits specified, by other oxides such as, for example, titanium oxide, tantalum oxide, niobium oxide and/or yttrium oxide. A proportion of up to 16% by weight of $Na_2O$ can be added for reasons of fusion technology. As a result, the fusion temperature of the mixture is reduced without impairment of the chemical stability.

A specific individual example of a precursor according to the invention has the following composition:
75.0% by weight of a radiopaque filler of the composition:
  54% by weight of $SiO_2$
  4% by weight of $B_2O_3$
  2% by weight of $Al_2O_3$
  5% by weight of $Gd_2O_3$
  22% by weight of SrO
  6% by weight of $La_2O_3$
  5% by weight of $Na_2O$
  2% by weight of CaO
2.0% by weight of Aerosil R 972 (highly disperse $SiO_2$)
16.0% by weight of bis-GMA
6.8% by weight of triethylene glycol dimethacrylate
0.09% by weight of camphor-quinone
0.11% by weight of N,N-dimethylaminoethyl methacrylate.

Curing is effected using the "Translux" light apparatus with a depth-curing filter from Messrs. Kulzer, the irradiation time being about 2 minutes. The composite material thus obtained has the following physical properties:
Flexural strength: 100 N/mm$^2$
Compressive strength: 270 MPa
Transparency (at a layer thickness of 3 mm): 20%
Radiopacity: 350%

We claim:

1. A composition for prosthesis purposes, comprising a polymerizable material and a radiopaque filler, wherein the radiopaque filler comprises an oxide of gadolinium and an oxide of strontium as a component combination which causes x-ray absorption.

2. A composition as claimed in claim 1, wherein the radiopaque filler further comprises an oxide of lanthanum.

3. A composition as claimed in claim 1, wherein the proportion of radiopaque filler is 20.0 to 90.0% by weight.

4. A composite material for producing a prosthesis, comprising a plastic binder and a radiopaque filler, wherein the radiopaque filler comprises:
(a) 1 to 31.0% by weight of $Gd_2O_3$
  7 to 32.0% by weight of SrO
  0 to 18% by weight of $La_2O_3$, the sum of the oxides $Gd_2O_3+SrO+La_2O_3$ being between 24.0 and 40.0% by weight,
(b) 14 to 62% by weight of $SiO_2$
  0 to 30% by weight of $B_2O_3$
  1 to 33% by weight of $Al_2O_3$ being between 42 and 75% by weight, and
(c) 0 to 16% by weight of $Na_2O$.

5. A composite material as claimed in claim 4, wherein the SrO proportion is partially replaced by
  (a) up to 18% by weight of CaO or
  (b) up to 5% by weight of MgO.

6. Composite material as claimed in claim 4, wherein the proportion of $Gd_2O_3$ and/or $La_2O_3$ and/or SrO is partially replaced up to 5% by weight by $ZrO_2$.

7. A composite material as claimed in claim 4, wherein the proportion of $Gd_2O_3$ and/or $La_2O_3$ and/or SrO is partially replaced up to 5% by weight by at least one of the the oxides $Y_2O_3$, $TiO_2$, $Ta_2O_5$ and $Nb_2O_5$.

8. A composite material as claimed in claim 4, wherein the radiopaque filler comprises:
  1.0–26.9% by weight of $Gd_2O_3$
  10.9–28.8% by weight of SrO
  0–12.0% by weight of $La_2O_3$
  16.1–58.0% by weight of $SiO_2$
  0–26.3% by weight of $B_2O_3$
  2.0–32.0% by weight of $Al_2O_3$
  0–16.0% by weight of $Na_2$
  0–15.0% by weight of CaO
  0–4.0% by weight of MgO
  0–5.0% by weight of $ZrO_2$ 0–5.0% by weight of $Y_2O_3$
0–4.0% by weight of $TiO_2$
0–5.0% by weight of $Ta_2O_5$
0–5.0% by weight of $Nb_2O_5$.

9. A composite material as claimed in claim 5, wherein the radiopaque filler comprises
2.0–10.0% by weight of $Gd_2O_3$
15.0–25.0% by weight of SrO
1.0–10.0% by weight of $La_2O_3$
50.0–60.0% by weight of $SiO_2$
2.0–6.0% by weight of $B_2O_3$
1.0–3.0% by weight of $Al_2O_3$
2.0–8.0% by weight of $Na_2O$
1.0–5.0% by weight of CaO.

10. A composite material as claimed in claim 4, wherein the radiopaque filler is in the form of a glass and has a refractive index of between 1.55 and 1.62.

11. A composite material as claimed in claim 4, wherein the radiopaque filler is in the form of glass ceramics.

12. A composite material as claimed in claim 4, wherein the radiopaque filler is in the form of a sintered product.

13. A composition as claimed in claim 1, wherein the radiopaque filler comprises a mixture of said oxides.

14. A composition as claimed in claim 1, further comprising a pigment having a particle size of less than 2 μm.

15. A composite material as claimed in claim 1, wherein the radiopaque filler is in the form of silanized particles.

16. A composition as claimed in claim 1, wherein the particle size of the radiopaque filler is 0.5 to 50 μm.

17. A composition as claimed in claim 1, which additionally contains up to 30% by weight of highly disperse silica and/or alumina.

18. A precursor for a composite material, comprising at least one polymerizable acrylate and/or methacryate as an organic binder and a radiopaque filler which comprises an oxide of gadolinium and an oxide of strontium.

19. A precursor as claimed in claim 18, which additionally contains a polymerization catalyst.

20. A precursor as claimed in claim 19, wherein the polymerization catalyst is a photopolymerization catalyst.

21. A dental material, comprising a composite material as claimed in claim 1.

22. A tooth-filling material, comprising a composite material as claimed in claim 1.

23. A dental material, comprising a precursor as claimed in claim 18.

24. A tooth-filling material, comprising a precursor as claimed in claim 18.

25. A bone cement, comprising a precursor as claimed in claim 18.

26. A precursor for a composite material as claimed in claim 18, wherein said radiopaque filler further includes compounds of lanthanum.

* * * * *